(12) United States Patent  
Craytor et al.

(10) Patent No.: US 11,857,451 B2
(45) Date of Patent: Jan. 2, 2024

(54) SHAPABLE POSTURE TRAINING DEVICE

(71) Applicant: BAKBON LLC, Boulder, CO (US)

(72) Inventors: Daniel Lee Craytor, Boulder, CO (US); Marc Andrew Hanchak, Denver, CO (US); Peter Schuyler Livingston, Denver, CO (US)

(73) Assignee: BAKBON LLC, Boulder, CO (US)

( * ) Notice: Subject to any disclaimer, the term of this patent is extended or adjusted under 35 U.S.C. 154(b) by 549 days.

(21) Appl. No.: 17/142,578

(22) Filed: Jan. 6, 2021

(65) Prior Publication Data

US 2021/0205112 A1 Jul. 8, 2021

Related U.S. Application Data

(60) Provisional application No. 62/957,785, filed on Jan. 6, 2020.

(51) Int. Cl.
*A61F 5/02* (2006.01)

(52) U.S. Cl.
CPC .............. *A61F 5/026* (2013.01); *A61F 5/028* (2013.01)

(58) Field of Classification Search
CPC ...... A61F 5/01; A61F 5/02; A61F 5/03; A61F 5/04; A61F 5/022; A61F 5/048; A61F 5/24; A61F 5/28; A61F 5/37; A61F 5/0104; A61F 2005/0144; A41C 1/00; A63B 21/4025

See application file for complete search history.

(56) References Cited

U.S. PATENT DOCUMENTS

| | | |
|---|---|---|
| 443,764 A | 12/1890 | Hilliard |
| 5,086,757 A | 2/1992 | Lestini |
| 5,156,605 A | 10/1992 | Pursley et al. |
| 5,199,940 A | 4/1993 | Morris et al. |
| 5,868,691 A | 2/1999 | Vishnevsky |
| 5,876,361 A | 3/1999 | Harris |
| 6,719,640 B1 | 4/2004 | Madole |
| 8,708,834 B1 | 4/2014 | Domangue |
| 9,295,896 B1 | 3/2016 | Hoang |
| 9,931,537 B2 | 4/2018 | Huebner |
| 2008/0228121 A1* | 9/2008 | Hughes .................. A61F 5/026 602/19 |

(Continued)

FOREIGN PATENT DOCUMENTS

| | | |
|---|---|---|
| CN | 2642268 | 9/2004 |
| GB | 2465424 A | 5/2010 |

*Primary Examiner* — George J Ulsh
*Assistant Examiner* — Andrew Jun-Wai Mok

(57) ABSTRACT

A shapable posture training device is disclosed herein. The posture training device can be shaped by hand to fit a wide variety of body shapes and postures and may address a variety of posture conditions. A shapable posture training device may include a pliable chassis configured to be worn against a thoracic spine region. The pliable chassis may include a shapable member that can be bent and shaped by hand. The pliable chassis may include a first rod receiver disposed in the pliable chassis and a second rod receiver disposed in the pliable chassis. The shapable member may extend from the first rod receiver to the second rod receiver. The shapable member may be bendable to alter alignment of a first centerline of a first bore of the first rod receiver and a second centerline of a second bore of the second rod receiver.

20 Claims, 17 Drawing Sheets

(56) References Cited

U.S. PATENT DOCUMENTS

2010/0204629 A1    8/2010  Specht
2013/0261520 A1  10/2013  Grenander
2015/0094633 A1    4/2015  Garcia
2015/0202072 A1*  7/2015  Glazener ............. A61F 5/05883
                                                          602/18

* cited by examiner

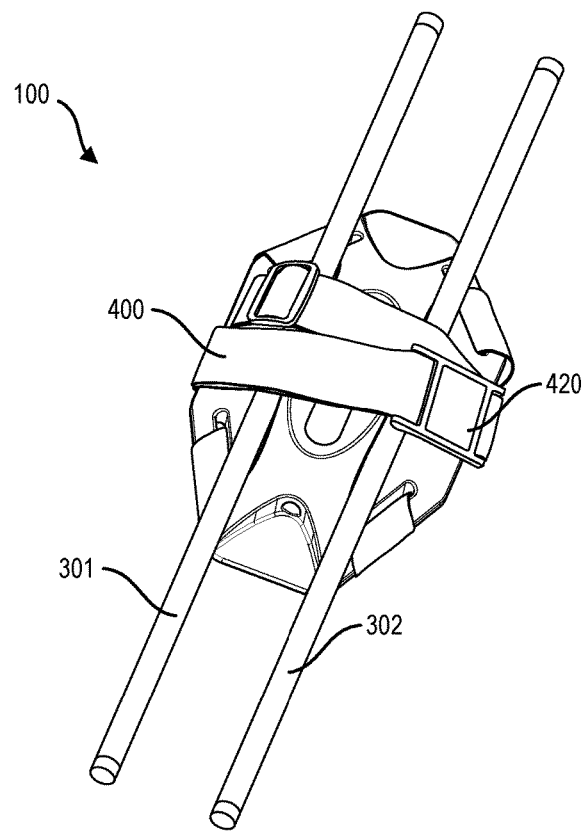
FIG. 4
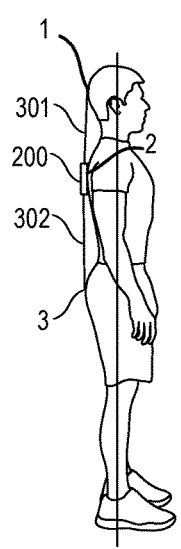 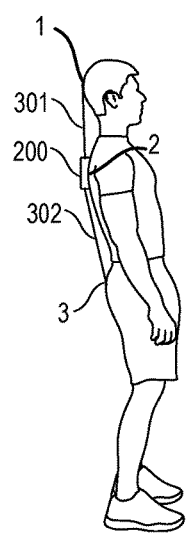 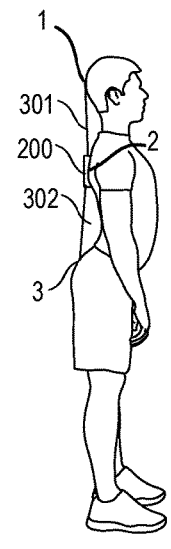 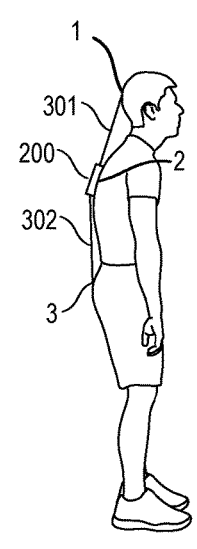 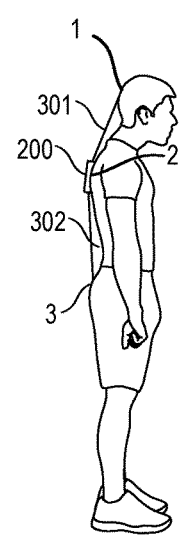
FIG. 5A   FIG. 5B   FIG. 5C   FIG. 5D   FIG. 5E

SECTION B-B

SECTION C-C

SECTION D-D

SECTION E-E

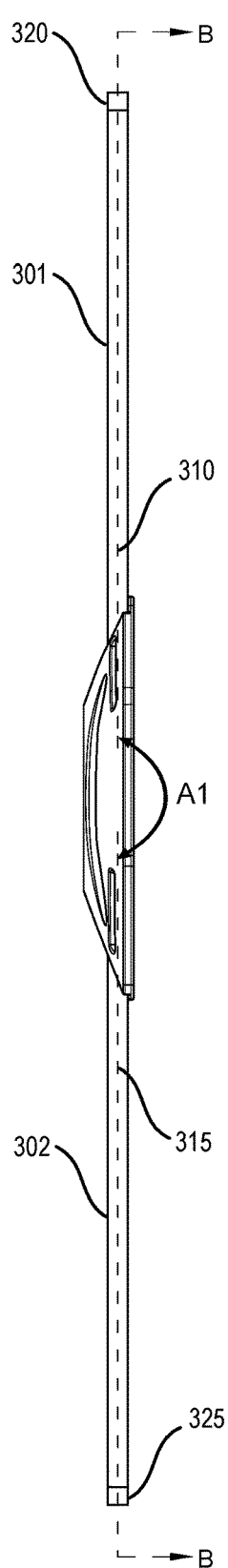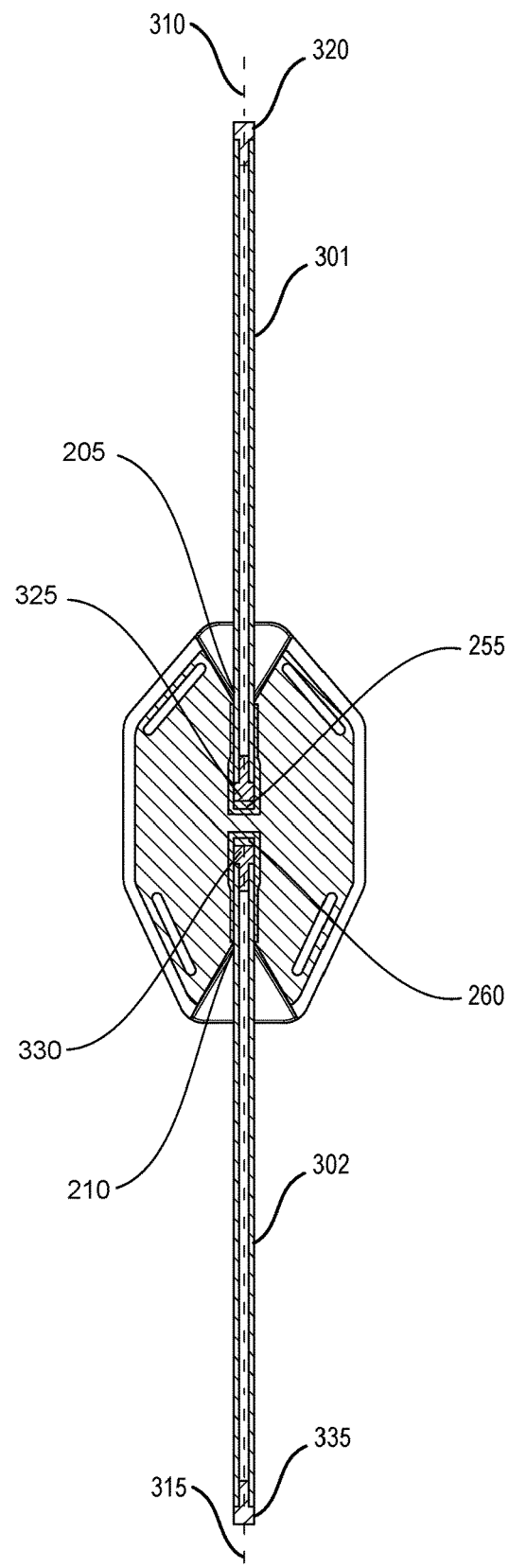
FIG. 14A
SECTION B-B
FIG. 14B

SHAPABLE POSTURE TRAINING DEVICE

FIELD

This disclosure relates to methods and apparatuses for improving posture. More specifically, this disclosure relates to posture training devices and methods that enable a person to achieve a neutral spine position.

CROSS REFERENCE

This application claims the benefit of U.S. Provisional Application No. 62/957,785, filed on Jan. 6, 2020, which is hereby incorporated by reference in its entirety.

BACKGROUND

A person may seek assistance from a physical therapist to improve their posture. The physical therapist may have the person perform certain physical movements. As the person performs the movements, the physical therapist may provide verbal and physical cues to help the person improve their posture and achieve a neutral spine.

A neutral spine is achieved when the lumbar spine curves inward, the thoracic spine curves outward, and the cervical spine curves slightly inward. To achieve a neutral spine, the therapist may have the person hold a wooden dowel, oriented vertically, against their back while performing movements. The wooden dowel is held in contact with three regions along the rear body. These regions are the 1) back of the head region, 2) mid-back region along the thoracic spine, and 3) sacrum region. When each of these regions is in contact with the wooden dowel, the person's spine may be in a neutral position. While performing movements, the person attempts to maintain contact with the wooden dowel at all three regions along their rear body.

The posture training method described above has at least four shortcomings. First, the method requires a physical therapist to observe the movements and provide cues to the person. The method does not allow the person to practice movements on their own (e.g. at home) between therapy sessions or in lieu of therapy sessions. Second, the method requires the person to hold the wooden dowel against their back as they perform physical movements, which may be challenging for individuals with limited flexibility or balance, such as elderly or injured patients. Third, the wooden dowel is long and inconvenient to store and transport. Fourth, the method requires the person's posture to be relatively good at the outset and require only minor correction.

FIG. 5A shows an example of good posture. FIGS. 5B-E show several examples of poor posture. While the wooden dowel method may be sufficient for a person with good or relatively good posture, the method may not work for someone with poor posture, since the wooden dowel may fail to simultaneously contact the back of head region 1, mid-back region 2, and sacrum region 3.

A new posture training device is needed to overcome the shortcomings of existing posture training devices and methods.

BRIEF DESCRIPTION OF THE DRAWINGS

FIG. 4 shows a front perspective view of the posture device of FIG. 1 in a disassembled and stowed configuration.

FIG. 5A shows an example of an individual exhibiting good posture and a neutral spine and wearing the posture training device.

FIG. 5B shows an example an individual exhibiting poor posture, known as sway back, and wearing the posture training device.

FIG. 5C shows an example of an individual exhibiting poor posture, known as lumbar lordosis, and wearing the posture training device.

FIG. 5D shows an example of an individual exhibiting poor posture, known as thoracic kyphosis, and wearing the posture training device.

FIG. 5E shows an example of an individual exhibiting poor posture, known as forward head, and wearing the posture training device.

FIG. 14A shows a side view of the posture training device.

FIG. 14B shows a cross-sectional front view of the posture training device of FIG. 14A taken along section B-B.

BRIEF SUMMARY

A posture training device and method is described herein. The posture training device allows an individual to assess and improve their posture to achieve a neutral spine. The device can be used independently, so it eliminates the need for a physical therapist or trainer to be present. Consequently, the device enables self-directed physical therapy and exercise.

Unlike a wooden dowel, the posture training device is hands-free, making it suitable for a wide variety of activities that require the use of hands, including weightlifting, practicing yoga, working (e.g. typing), running, cycling, and swimming. Consequently, the posture training device allows posture training to be incorporated into a person's preferred activities or workday rather than requiring separate posture-only training sessions.

The posture training device is shapable by hand to conform to a wide variety of body shapes and posture conditions. The device is compact and easy to store. The device is comfortable to wear for extended periods of time, such as during long workout sessions.

The posture training device may be suitable for individuals suffering from poor posture conditions, such as sway back, lumbar lordosis, thoracic kyphosis, and forward head posture, who are seeking to improve their posture. The device may also be suitable for individuals with good posture who are seeking to maintain or improve their posture while performing their favorite activities. For example, the device may be suitable for endurance athletes who are seeking to maintain correct posture during extended exercise sessions as a way of reducing fatigue, reducing discomfort, and/or improving performance.

The posture training device may include a chassis. The chassis may include a pliable body that is worn against a user's thoracic spine region. The device may include a first rod extending upward from the chassis and contacting the user's back of head region. The device may include a second rod extending downward from the chassis and contacting the user's sacrum region. Through physical contact provided by the pliable body, first rod, and second rod, the device may establish three regions of contact along a user's rear body.

The pliable body may include an internal shapable member. Adjusting the shapable member may alter a rear surface contour of the pliable body to match a user's unique physical contour along their mid-back region. Adjusting the shapable member may adjust a relative angle between the first and second rods to further tailor the device to fit the user's unique physical contour. Consequently, regardless of whether the user has good or poor posture, the device can be adjusted to contact three regions along the user's rear body and serve as an effective posture training device. As the user's posture improves over time, the shapable member may be periodically adjusted to match the user's changing physical shape to encourage progressive posture improvement.

DETAILED DESCRIPTION

Figure 6:
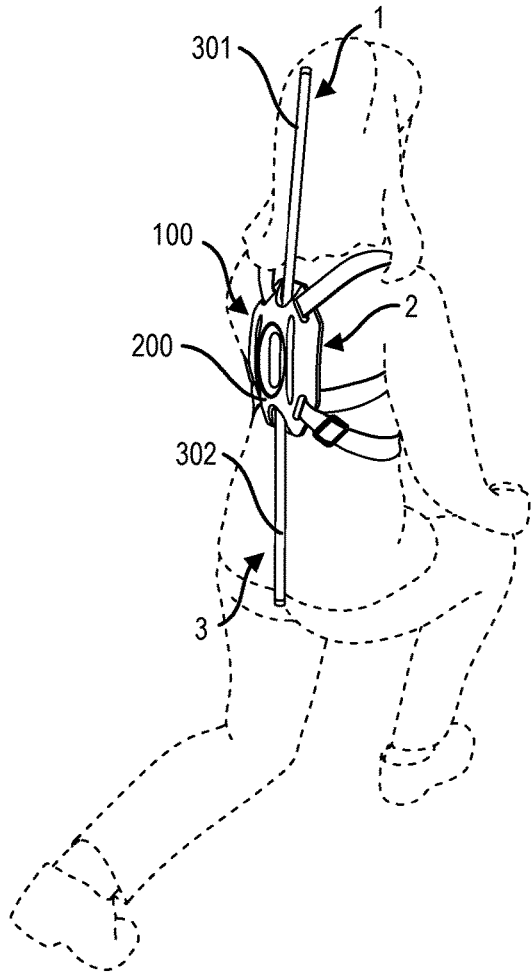
FIG. 6 shows a person performing a lunge while wearing the posture training device.
Figure 7:
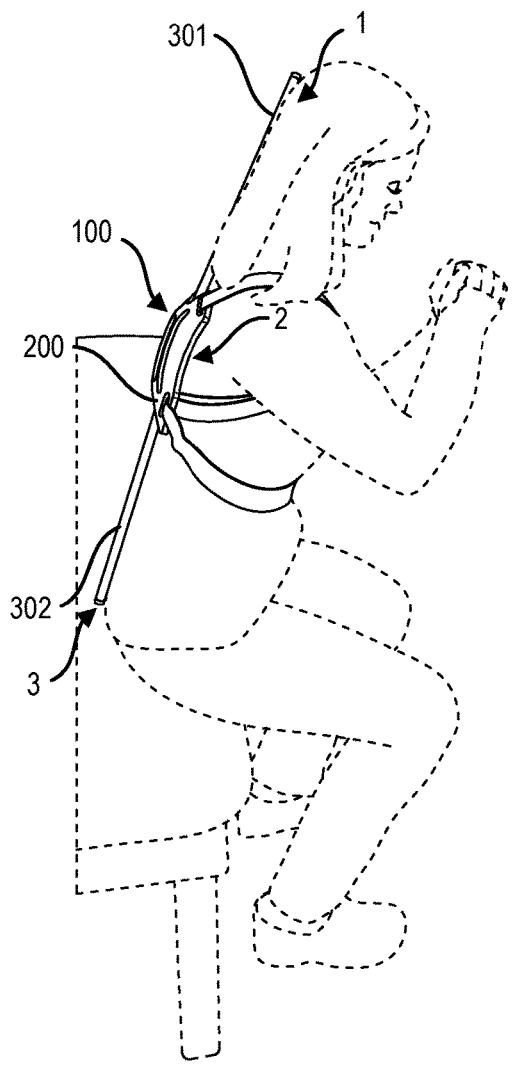
FIG. 7 shows a person performing a squat while wearing the posture training device.
Figure 8:
FIG. 8 shows a person lifting a hand weight while wearing the posture training device.
Figure 9:
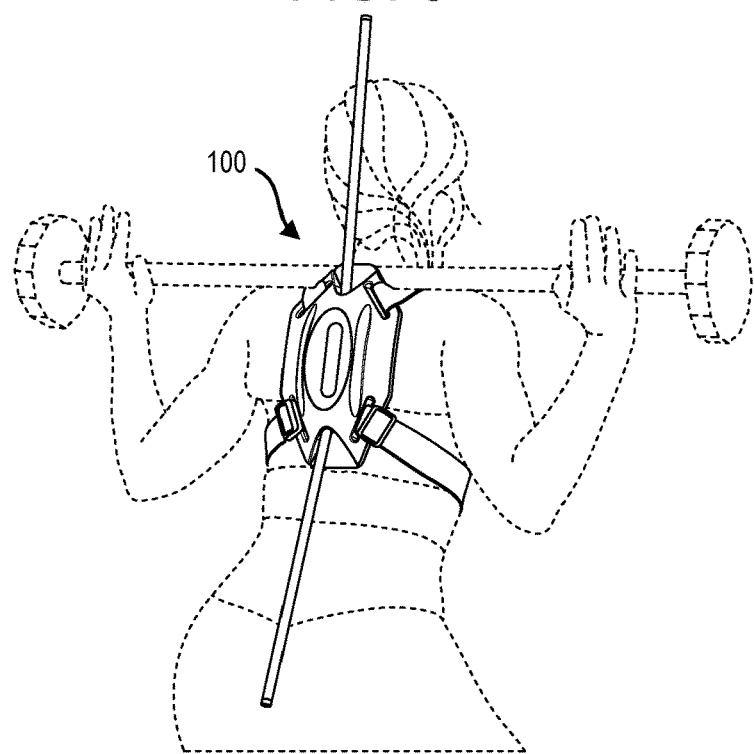
FIG. 9 shows a person performing a squat while wearing the posture training device.
Figure 10:
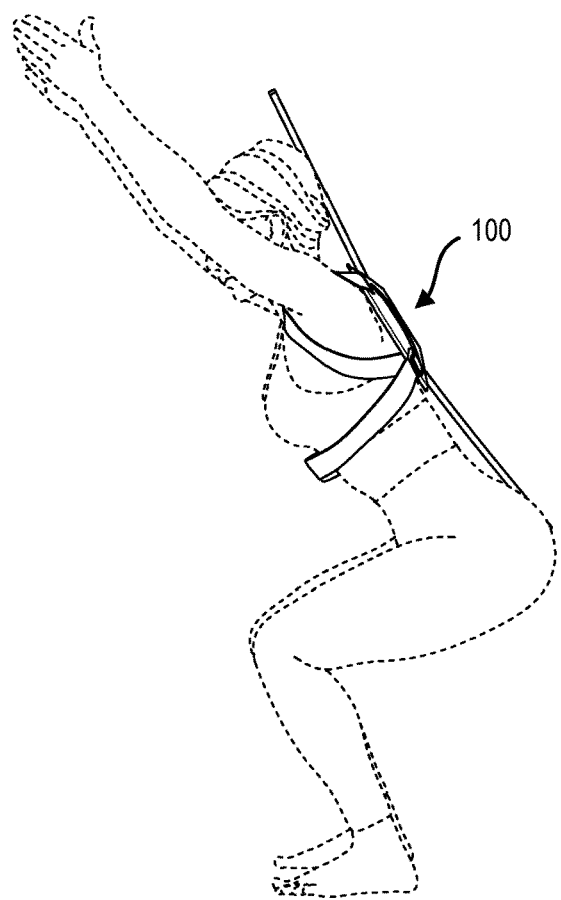
FIG. 10 shows a person practicing yoga while wearing the posture training device.
Figure 11:
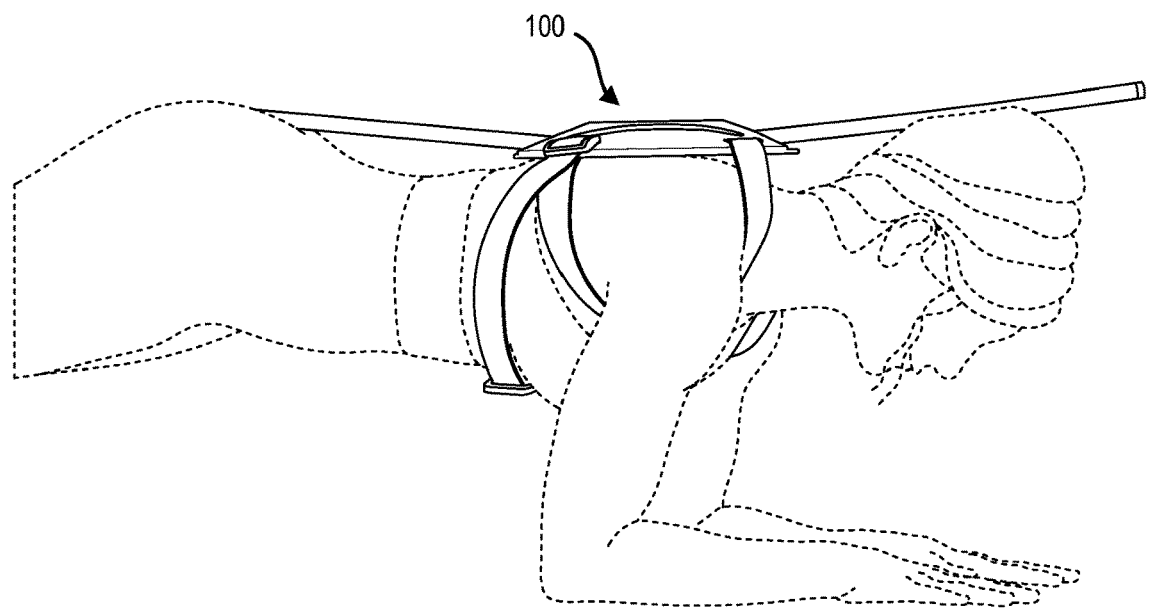
FIG. 11 shows a person practicing a plank while wearing the posture training device.

A shapable posture training device 100 is shown in the figures and described herein. The posture training device 100 is configured to contact a back of head region 1, a mid-back region 2, and a sacrum region 3, thereby providing three regions of contact along a user's spine, as shown in FIGS. 6 and 7. The posture training device 100 provides tactile feedback for postural alignment, thereby enabling the user to independently monitor and, if necessary, correct their posture to achieve a neutral spine position. The posture training device 100 can be worn, for example, during everyday activities or workout sessions, thereby allowing posture training to be incorporated into a user's daily routine. In addition to saving time and expense by avoiding sessions with a physical therapist, incorporating posture training into daily activities, such as biking, swimming, and yoga, may provide health and performance benefits that exceed those achievable with conventional methods.

Figure 13A:
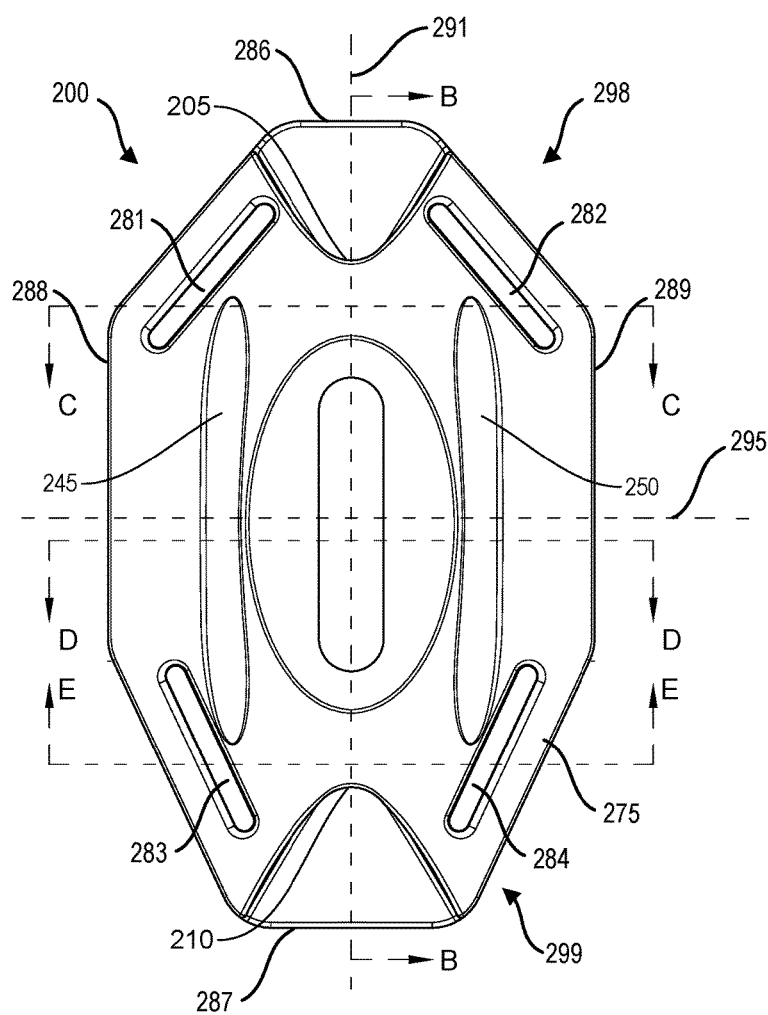
FIG. 13A shows a top view of the chassis of the posture training device.

The posture training device 100 may include a chassis 200. The chassis 200 may be worn against a user's thoracic spine (mid-back) region 2 during use, as shown in FIGS. 6 and 7. The chassis 200 may include a pliable body 275. The pliable body may have a top side 286, a bottom side 287, a left side 288, a right side 289, a horizontal midplane 295, and a vertical midplane 291, as shown in FIG. 13A. The pliable body 275 may have a top portion 298 located between the horizontal midplane 295 and the top side 286. The pliable body 275 may have bottom portion 299 located between the horizontal midplane 295 and the bottom side 287. The pliable body 275 may have a middle portion 279 located proximate to the horizontal midplane 295.

The pliable body 275 may be made of, for example, ethylene-vinyl acetate (EVA) closed cell foam, chloroprene rubber (CR), styrene-butadiene rubber (SBR), or ethylene-propylene-diene-monomer (EPDM). These examples are not limiting. The pliable body 275 may have a rear surface 280 that fits comfortably against a user's mid-back region 2.

Figure 12:
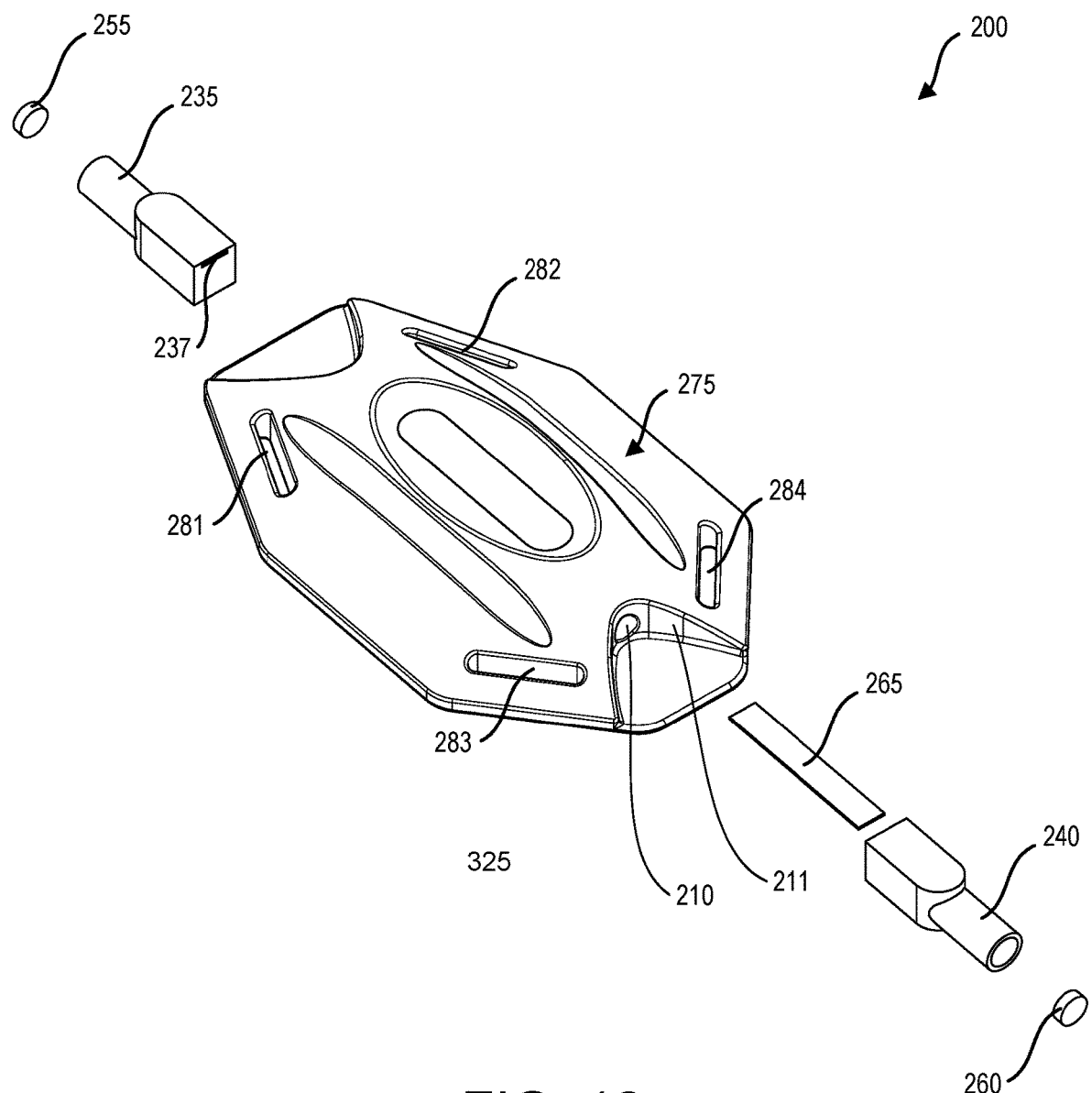
FIG. 12 shows an exploded view of a chassis of the posture training device.
Figure 13B:
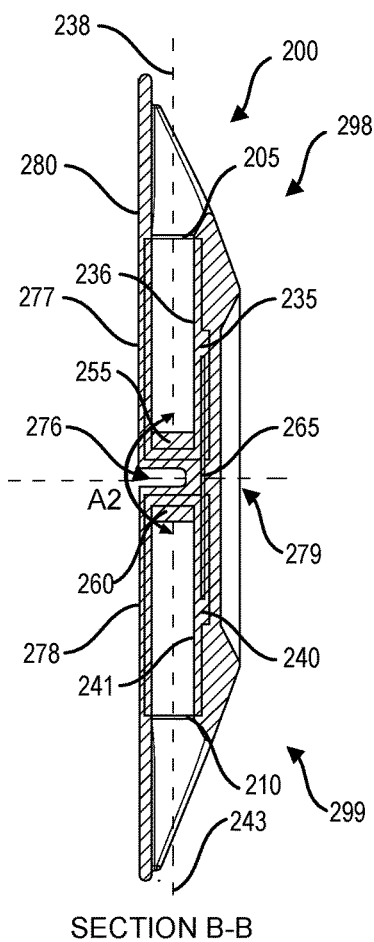
FIG. 13B shows a cross-sectional side view of the chassis of FIG. 13A taken along section B-B.
Figure 13C:
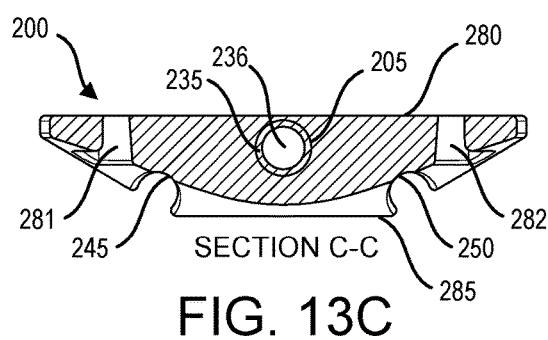
FIG. 13C shows a cross-sectional top view of the chassis of FIG. 13A taken along section C-C.
Figure 13D:
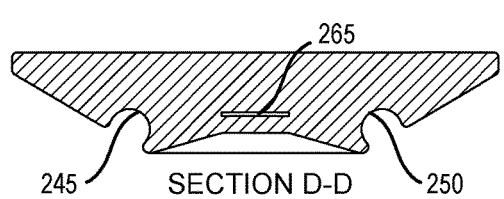
FIG. 13D shows a cross-sectional top view of the chassis of FIG. 13A taken along section D-D.

The chassis 200 may include a shapable member 265. The shapable member 265 may be disposed within the pliable body 275. FIG. 12 shows an exploded view of the chassis 200 and internal components, including the shapable member 265. FIG. 13B shows a cross-sectional view of the chassis 200 and reveals positioning of the shapable member 265 within the chassis 200. In some examples, the shapable member 265 may be a metal member (e.g. a metal strip, plate, or rod) that is capable of repeatedly bending and assuming new positions without breaking. In other examples, the shapable member 265 may be a polymer member that is capable of repeatedly bending and taking on new positions without breaking. The shapable member 265 may be capable of bending and assuming new positions hundreds or thousands of times over the lifecycle of the device, thereby allowing the user to reshape the device 100 every time it is worn without failure of the shapable member.

Figure 24:
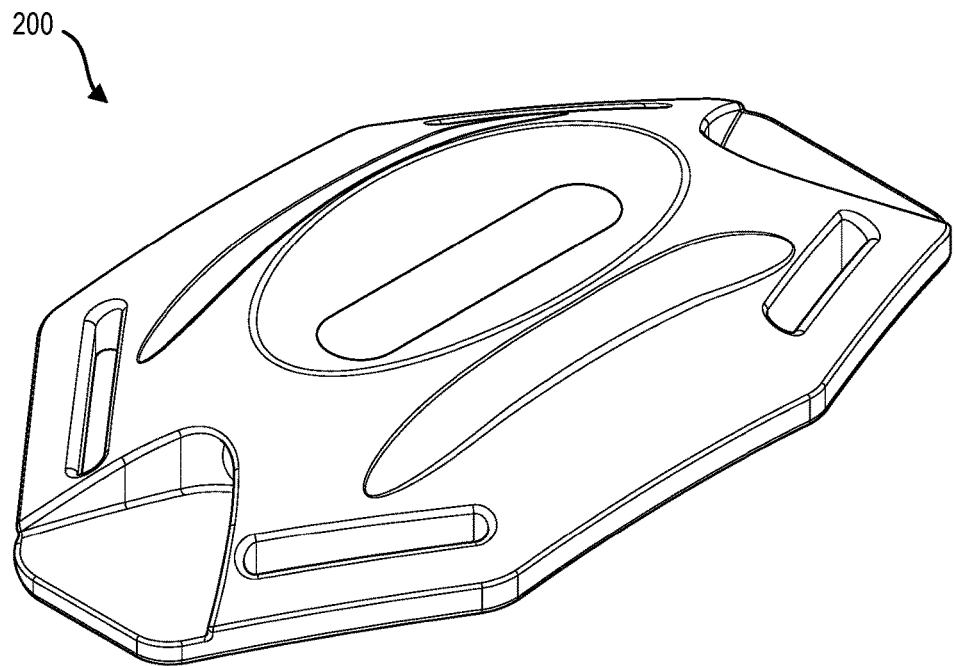
FIG. 24 shows a front perspective view of the chassis of FIG. 15 in a curved configuration.
Figure 25:
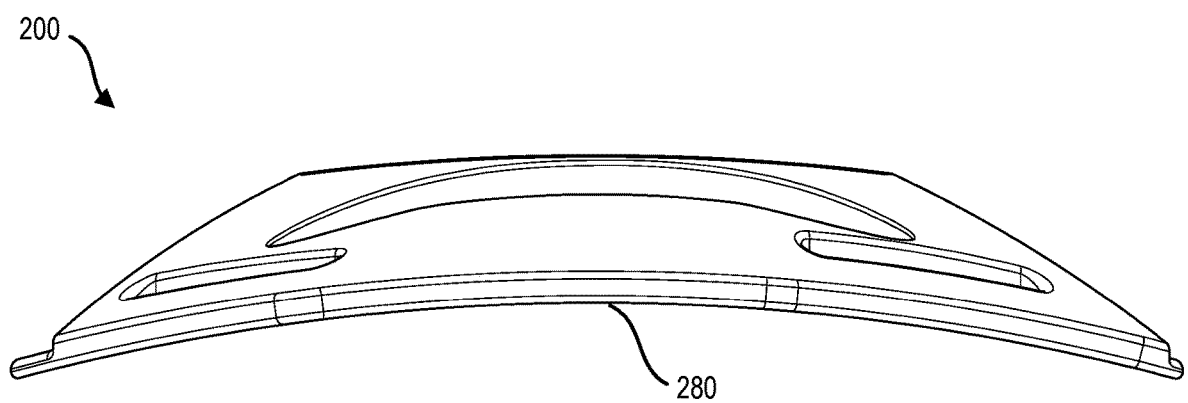
FIG. 25 shows a side view of the chassis of FIG. 15 in a curved configuration.
Figure 26A:
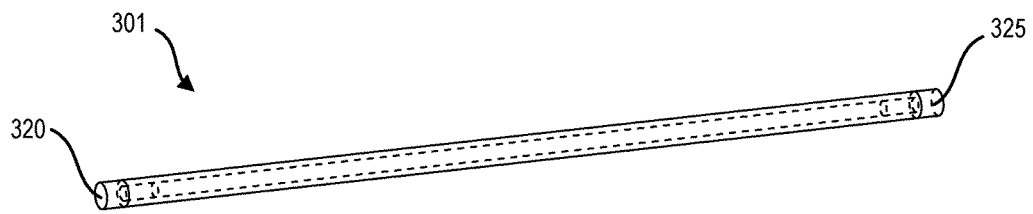
FIG. 26A shows a perspective view of a rod of the posture training device of FIG. 15.
Figure 26B:
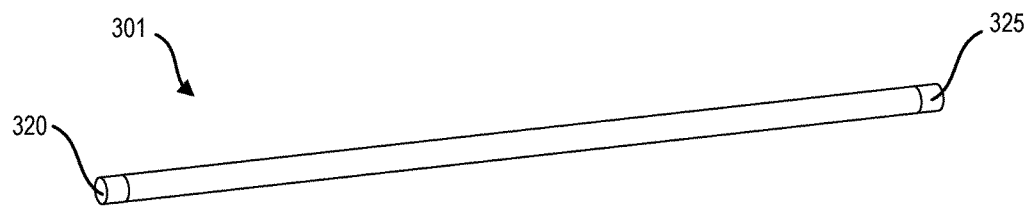
FIG. 26B shows a perspective view of a rod of the posture training device of FIG. 15.
Figure 26C:
FIG. 26C shows an exploded view of the rod of the posture training device of FIG. 15.

The shapable member 265 may extend lengthwise within the chassis (e.g. from a top half of the chassis 200 to a bottom half of the chassis, as shown in FIG. 13B). By bending the shapable member 265, the chassis 200 may be transitioned from a flat configuration, as shown in FIGS. 16-21, to a curved configuration, as shown in FIGS. 24 and 25, that conforms to a user's mid-back region 2. Each user may have a unique curvature along their mid-back to which the chassis 200 conforms to provide a proper fit. As a user's posture improves with training and exercise, the curvature of the chassis 200 may need to be manually adjusted to match changes in posture. The shapable member 265 allows the shape of the chassis 200 to be adjusted manually by hand to fit a wide variety of body shapes. By applying a bending force to the chassis 200, the shapable member 265 within the chassis may be altered from flat to curved, resulting in the rear surface 280 of the chassis 200 transitioning from a flat surface to a contoured rear surface.

As shown in FIG. 14B, the posture training device 100 may include a first removable rod 301. The posture training device 100 may include a second removable rod 302. The first and second rods (301, 302) may be separate rods that are removably insertable into respective rod receivers (235, 240) in the chassis 200. Having separate rods, instead of a single rod, may allow shorter rods to be used, which renders the posture training device 100 more compact when in a stowed configuration, as shown in FIG. 4, and allows the device 100 to fit within a duffel bag or backpack.

As shown in FIGS. 5-7, when the chassis 200 is worn against the user's mid-back region, the first rod 301 may extend from the chassis 200 to a back surface of the user's head 1, and the second rod 302 may extend from the chassis 200 to the user's sacrum region 3, thereby establishing three regions of contact along the user's rear body.

FIG. 5A shows an individual with good posture wearing the posture training device 100. FIGS. 5B-5E show four examples of individuals with poor posture wearing the posture training device 100. Three contact regions are shown along the rear body of each individual and correspond to the three regions the device 100 contacts during use. The three regions are the back of head region 1, thoracic spine region 2, and sacrum region 3. As shown in FIGS. 5A-5E, the posture training device 100 may be adjusted to accommodate a wide variety of posture conditions.

A relative rod angle A1 is formed at an intersection between a first centerline 310 of the first rod 301 and a second centerline 315 of the second rod 302, as shown in FIG. 14A. For a user with good posture and a neutral spine, as shown in FIG. 5A, the relative rod angle may be about 180 degrees. To meet the needs of certain poor posture conditions, the posture training device 100 may be adjustable to provide a relative rod angle less than 180 degrees (i.e. θ<180°), as shown in FIG. 5E. Conversely, the posture training device 100 may be adjustable to provide a relative rod angle greater than 180° (i.e. θ>180°) to meet the needs of user's suffering from conditions such as lumbar lordosis, as shown in FIG. 5C.

In one example, the shapable member 265 may be bendable to provide relative rod angles A1 ranging from about 135 degrees to about 225 degrees. In another example, the shapable member 265 may be bendable to provide relative rod angles A1 ranging from about 145 degrees to about 215 degrees. In another example, the shapable member 265 may be bendable to provide relative rod angles A1 ranging from about 155 degrees to about 205 degrees. In another example, the shapable member 265 may be bendable to provide relative rod angles A1 ranging from about 165 degrees to about 195 degrees.

FIG. 14B shows a cross-sectional view of the posture training device 100 having two rods. The first rod 301 may be inserted into a first opening 205 in the chassis 200 proximate to a top side of the chassis. The second rod 302 may be inserted into a second opening 210 proximate to the bottom side of the chassis 200.

The chassis 200 may include a first guide wall 206 that guides the first rod 301 into the first opening 205. The first guide wall 206 may have a funnel shape. The first guide wall 206 may have a substantially parabolic shape with the first opening 205 located at or near a vertex of the parabolic shape. The chassis 200 may include a second guide wall 211 that guides the second rod 302 into the second opening 210. The second guide wall 211 may have a funnel shape. The second guide wall 211 may have a substantially parabolic shape with the second opening 210 located at or near a vertex of the parabolic shape.

The first opening 205 may include a first rod receiver 235, as shown in FIGS. 12 and 13B. The first rod receiver 235 may include a bore 236 to receive the first rod 301. The second opening 210 may include a second rod receiver 240, as shown in FIGS. 12 and 13B. The second rod receiver 240 may include a second bore 241 to receive the second rod 302.

The first rod receiver 235 may include a first magnet 255, as shown in FIGS. 12 and 13B. The first magnet 255 may exert an attractive magnetic force on a ferrous end 325 of the first rod 301 that holds the first rod in place, as shown in FIG. 14B. The second rod receiver 240 may include a second magnet 260, as shown in FIGS. 12 and 13B. The second magnet 260 may exert an attractive magnetic force on a ferrous end 330 of the second rod 302 that holds the first rod in place, as shown in FIG. 14B. In one example, the ferrous ends may be steel screws threaded into respective ends of the rods.

The rods (301, 302) may be interchangeable and reversible in orientation. Accordingly, the first rod 301 may include a second ferrous end 320, and the second rod 302 may include a second ferrous end 335, as shown in FIG. 14B.

As shown in FIG. 13B, the first rod receiver 235 may be located in a top portion 298 (e.g. top half) of the chassis 200, and the second rod receiver 240 may be located in a bottom portion 299 (e.g. bottom half) of the chassis. The first rod receiver 235 may include a first slot 237 to receive a first end of the shapable member 265, as shown in FIGS. 12 and 13B. The second rod receiver 240 may include a second slot 242 to receive a second end of the shapable member 265. Bending the shapable member 265 may result in intentional misalignment of a first bore centerline 238 of the first bore 236 and the second bore centerline 243 of the second bore 241. As a result, and depending on the direction of the bend, an intersection of the first bore centerline 238 and the second bore centerline 243 may form a relative bore angle A2 that is greater than 180 degrees, less than 180 degrees, or about 180 degrees as shown in FIG. 13B. In one example, the shapable member 265 may be bendable to provide relative bore angles A2 ranging from about 135 degrees to about 225 degrees. In another example, the shapable member 265 may be bendable to provide relative bore angles A2 ranging from about 145 degrees to about 215 degrees. In another example, the shapable member 265 may be bendable to provide relative bore angles A2 ranging from about 155 degrees to about 205 degrees. In another example, the shapable member 265 may be bendable to provide relative bore angles A2 ranging from about 165 degrees to about 195 degrees.

Figure 15:
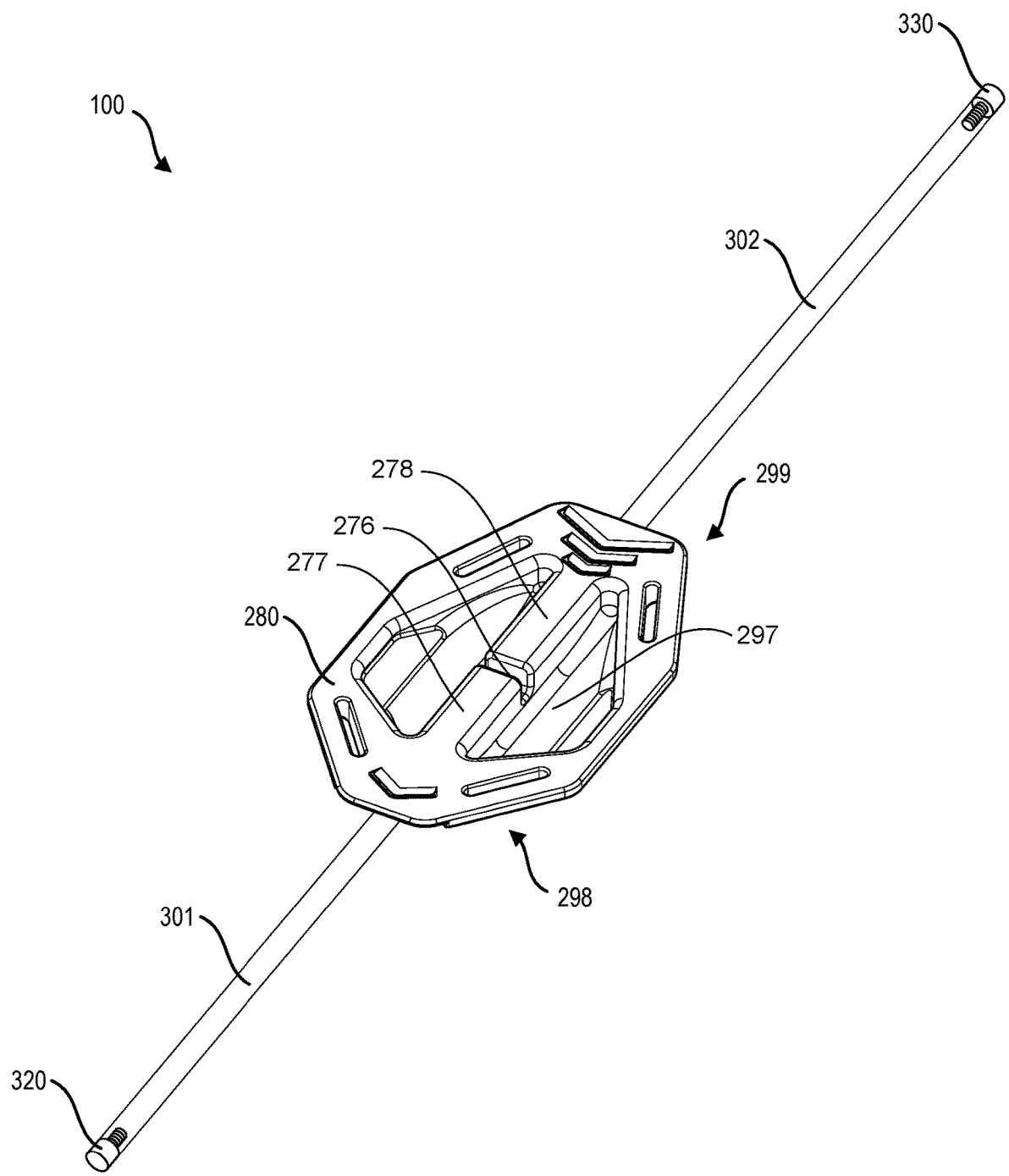
FIG. 15 shows a rear perspective view of a posture training device.
Figure 16:
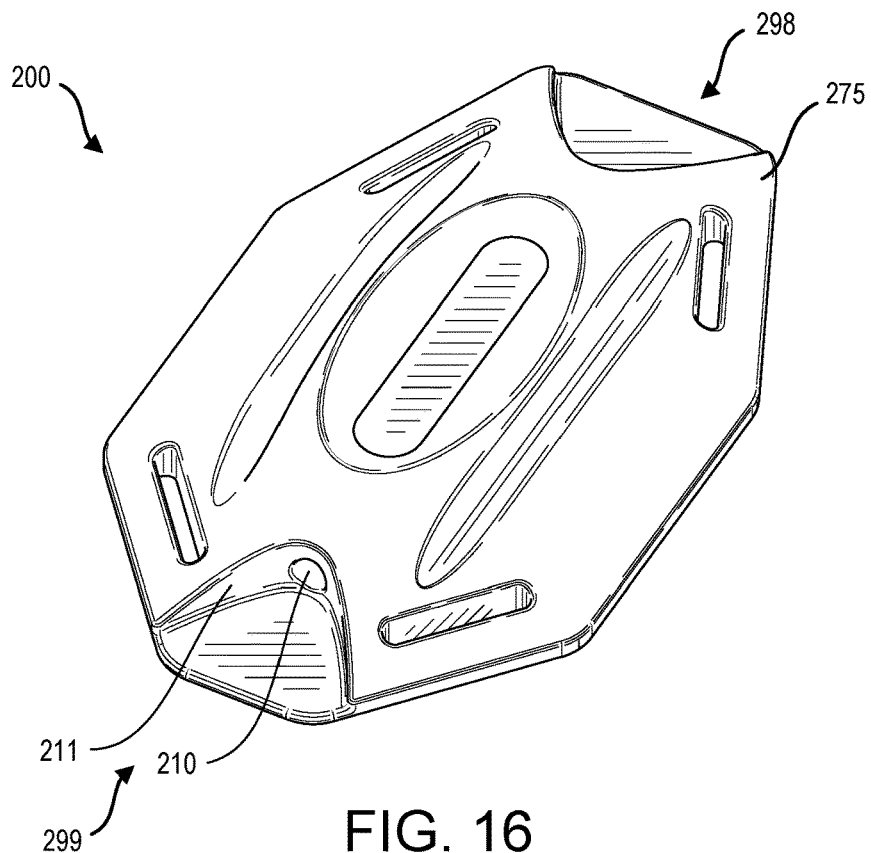
FIG. 16 shows a front perspective view of the chassis of the posture training device of FIG. 15.

The pliable body 275 may include a first beam 277 extending lengthwise along a rear surface 280 of the pliable body, as shown in FIG. 15. The first beam 277 may extend vertically from a top portion 298 of the pliable body to a middle portion 279 of the pliable body 275. The first beam 277 may enhance the structural integrity of the pliable body 275. The first beam 277 may cover the first rod receiver 235 with a pliable material and enhance comfort by providing a pliable covering over the rigid rod receiver.

The pliable body 275 may include a second beam 278 extending lengthwise along a rear surface 280 of the pliable body, as shown in FIG. 15. The second beam 278 may extend vertically from a bottom portion 299 of the pliable body to a middle portion 279 of the pliable body 275. The second beam 278 may enhance the structural integrity of the pliable body 275. The second beam 278 may cover the second rod receiver 240 with a pliable material and enhance user comfort by providing a pliable covering over the rigid rod receiver.

Figure 17:
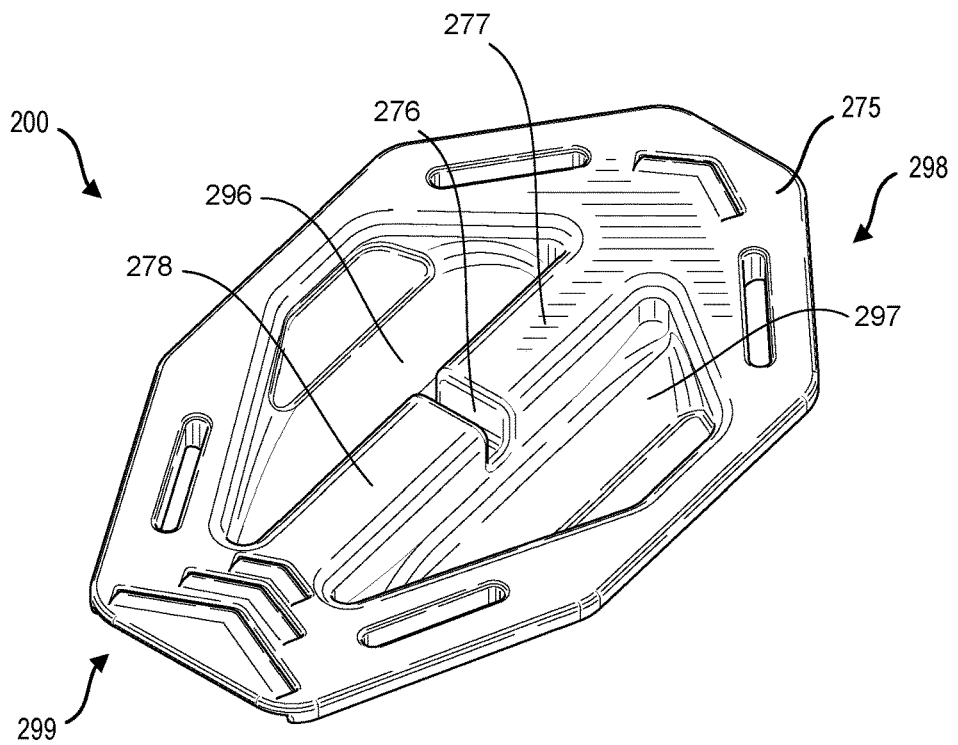
FIG. 17 shows a rear perspective view of the chassis of FIG. 15.
Figure 18:
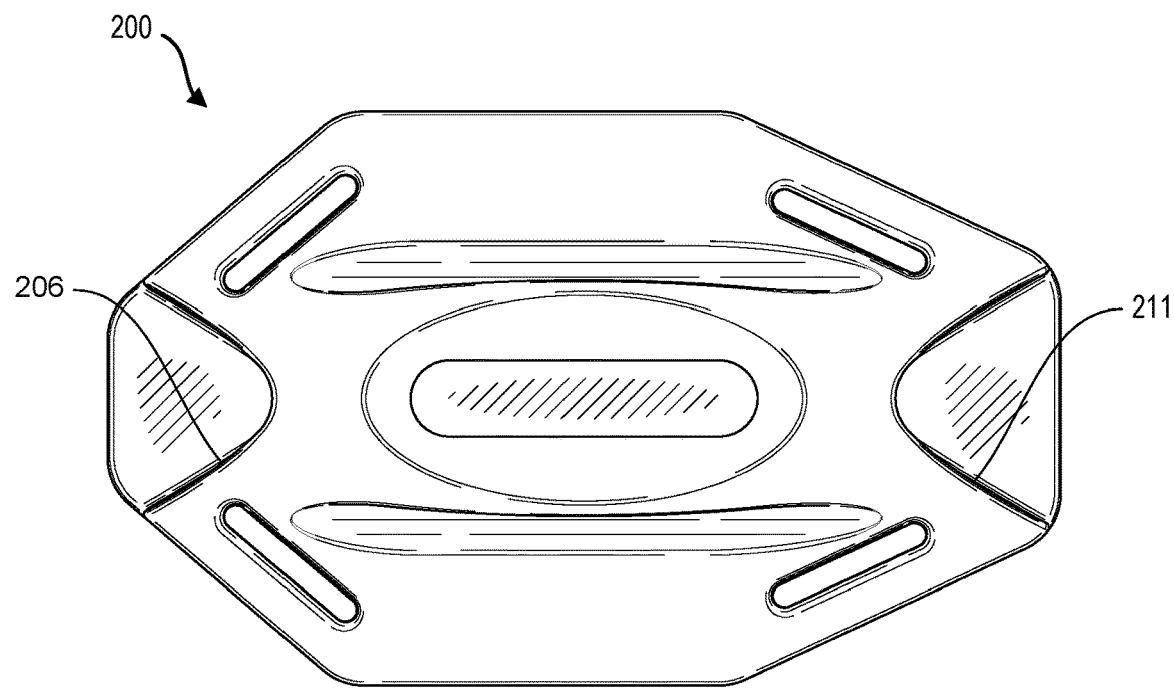
FIG. 18 shows a front view of the chassis of FIG. 15.
Figure 19:
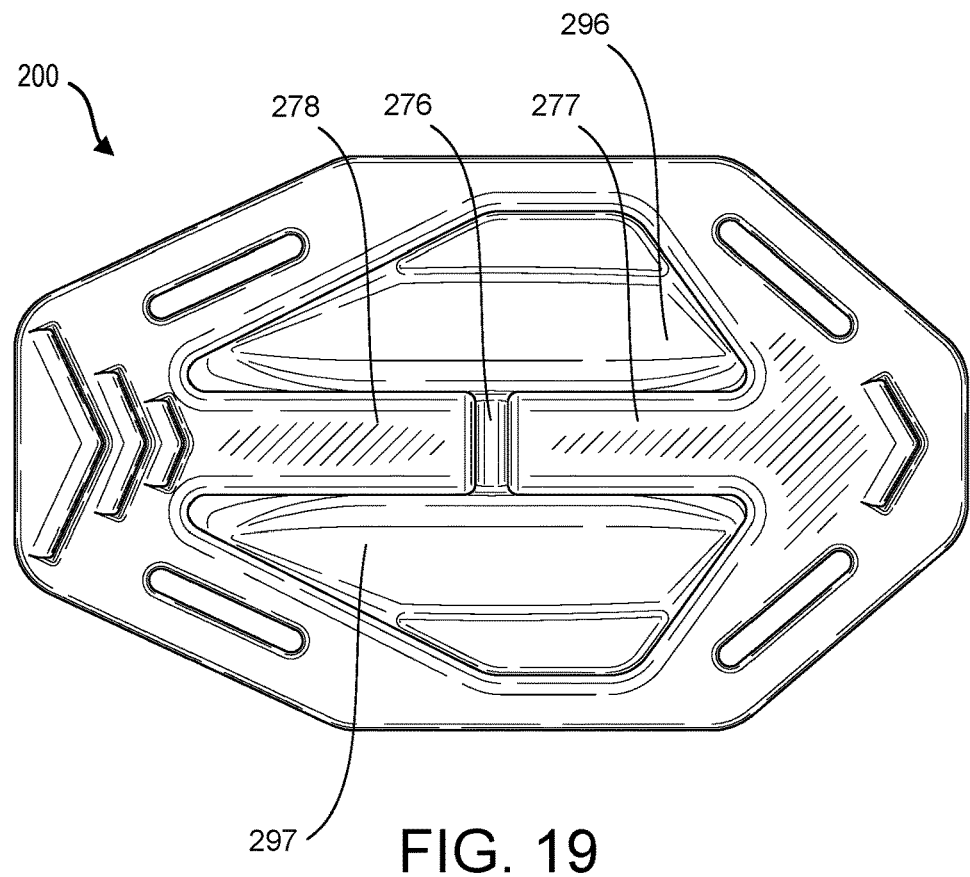
FIG. 19 shows a rear view of the chassis of FIG. 15.
Figure 20:
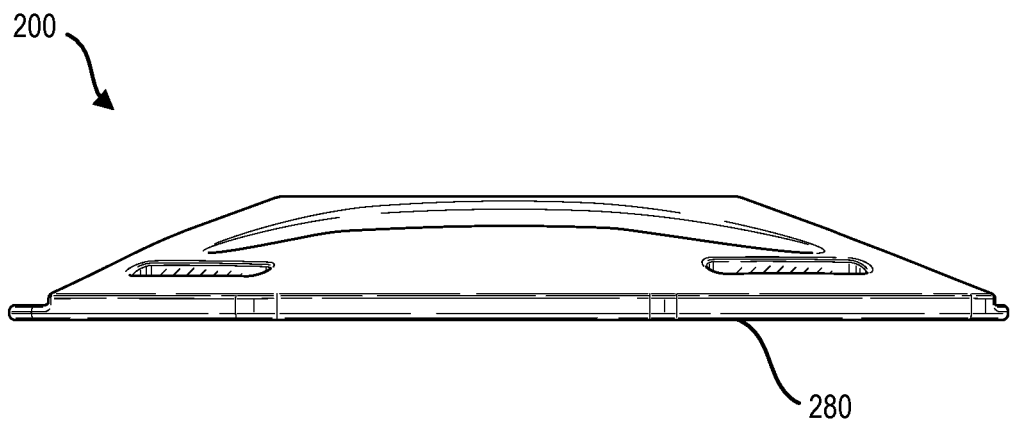
FIG. 20 shows a side view of the chassis of FIG. 15 in a flat configuration.
Figure 21:
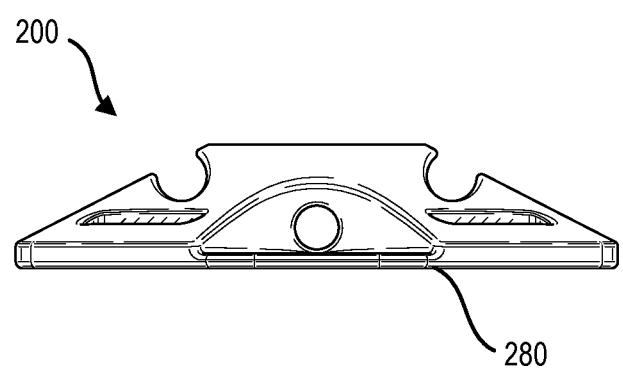
FIG. 21 shows a top view of the chassis of FIG. 15.
Figure 22:
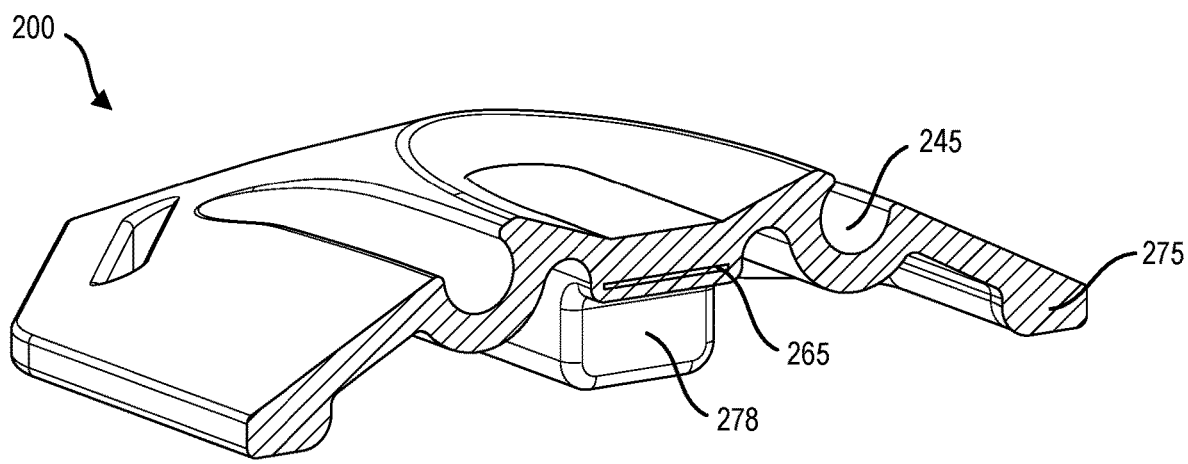
FIG. 22 shows a cross-sectional view of the chassis of FIG. 15.
Figure 23:
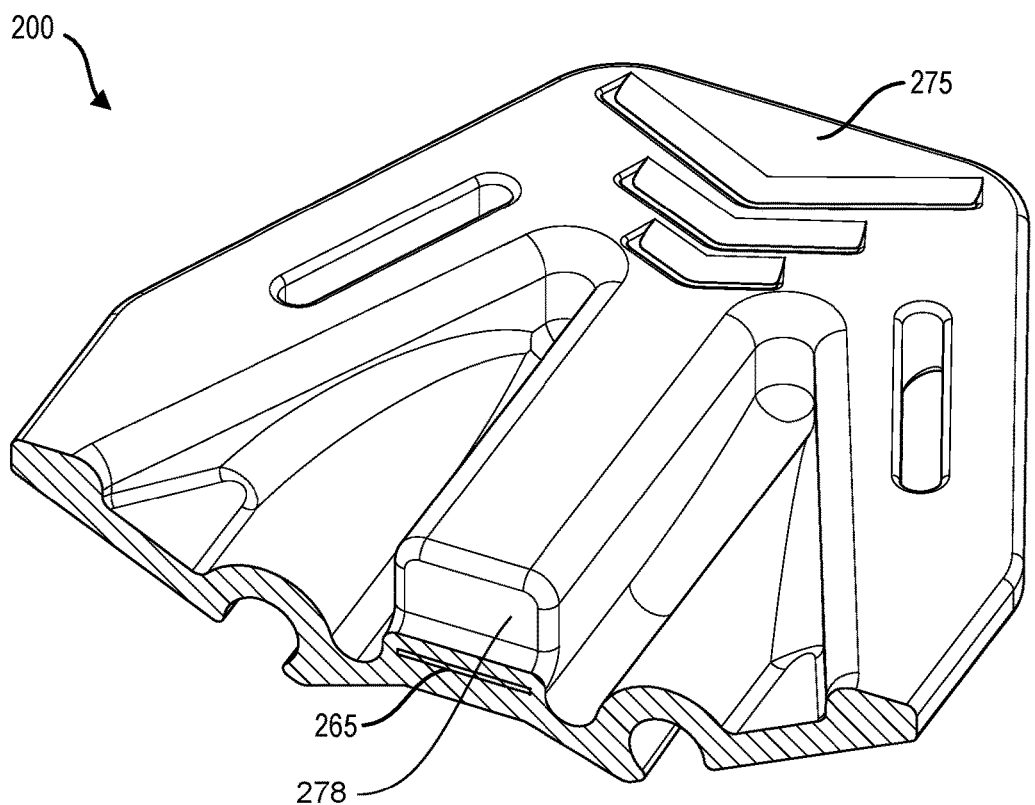
FIG. 23 shows a cross-sectional view of the chassis of FIG. 15.

The pliable body 275 may include one or more airflow features, such as one or more vents, louvers, or pockets to permit air exchange and prevent buildup of perspiration between the chassis 200 and the user's back. FIG. 17 shows a first rear pocket 296 and a second rear pocket 297 formed in the rear surface 280 of the pliable body 275. The first rear pocket 296 may extend from a top portion 298 of the pliable body to a bottom portion 299 of the pliable body. The second rear pocket 297 may extend from a top portion 298 of the pliable body to a bottom portion 299 of the pliable body. In addition to improving airflow, the first and second pockets (296, 297) may enhance bendability of the pliable body by reducing bending resistance created by the material of the pliable body.

The pliable body 275 may include a rear channel 276 located between the first rod receiver 235 and the second rod receiver 240, as shown in FIGS. 13B and 17. The rear channel 276 may allow the pliable body 275 to more easily bend to match a user's unique physical shape. The rear channel 276 may extend from the first rear pocket 296 to the second rear pocket 297. The rear channel 276 may extend substantially horizontally across the rear surface 280 of the pliable body 275. The rear channel 276 may permit bending of the pliable body 275 without interference between the first rod receiver 235 and the second rod receiver 240. The rear channel 276 may permit bending of the pliable body 275 without interference between the first beam 277 and the second beam 278. The rear channel 276 may be at least 0.25 inch wide. The rear channel 276 may be at least 0.5 inch wide. The rear channel 276 may be at least 0.75 inch wide. The rear channel may be at least 1.0 inch wide.

Figure 13E:
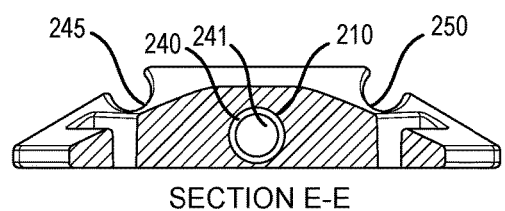
FIG. 13E shows a cross-sectional bottom view of the chassis of FIG. 13A taken along section E-E.

As shown in FIG. 13E, the chassis 200 may include a first rod storage slot 245 configured to receive and retain the first rod 301. The first rod storage slot 245 may be formed in a front surface 285 of the pliable body 275. The first rod storage slot 245 may retain the first rod 301 through a friction fit. The chassis 200 may include a second rod storage slot 250 configured to receive and retain the second rod 302. The second rod storage slot 250 may be formed in the front surface 285 of the pliable body 275. The second rod storage slot 250 may retain the second rod 302 through a friction fit.

The pliable body 275 may include a plurality of strap slots configured to receive a wearable strap. A first strap slot 281 may be located between the horizontal midplane 295 and the top side 286 and between a vertical midplane 291 and a left side 288, as show in FIG. 13A. A second strap slot 282 may be located between the horizontal midplane 295 and the top side 286 and between the vertical midplane 291 and a right side 289. A third strap slot 283 may be located between the horizontal midplane 295 and the bottom side 287 and between the vertical midplane 291 and the left side 288. A fourth strap slot 284 may be located between the horizontal midplane 295 and the bottom side 287 and between the vertical midplane 291 and the right side 289.

Figure 1:
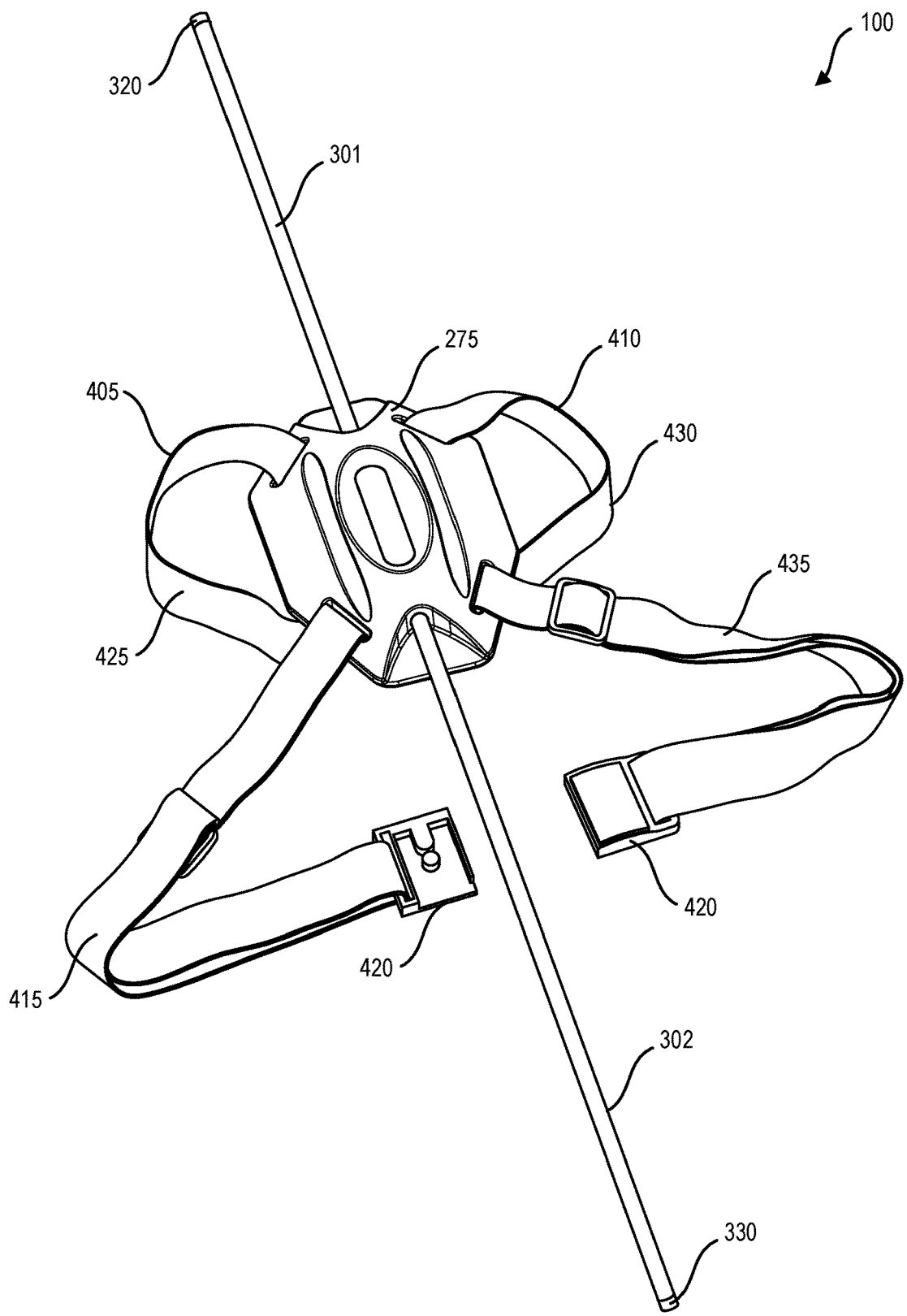
FIG. 1 shows a front perspective view of a posture training device.
Figure 2:
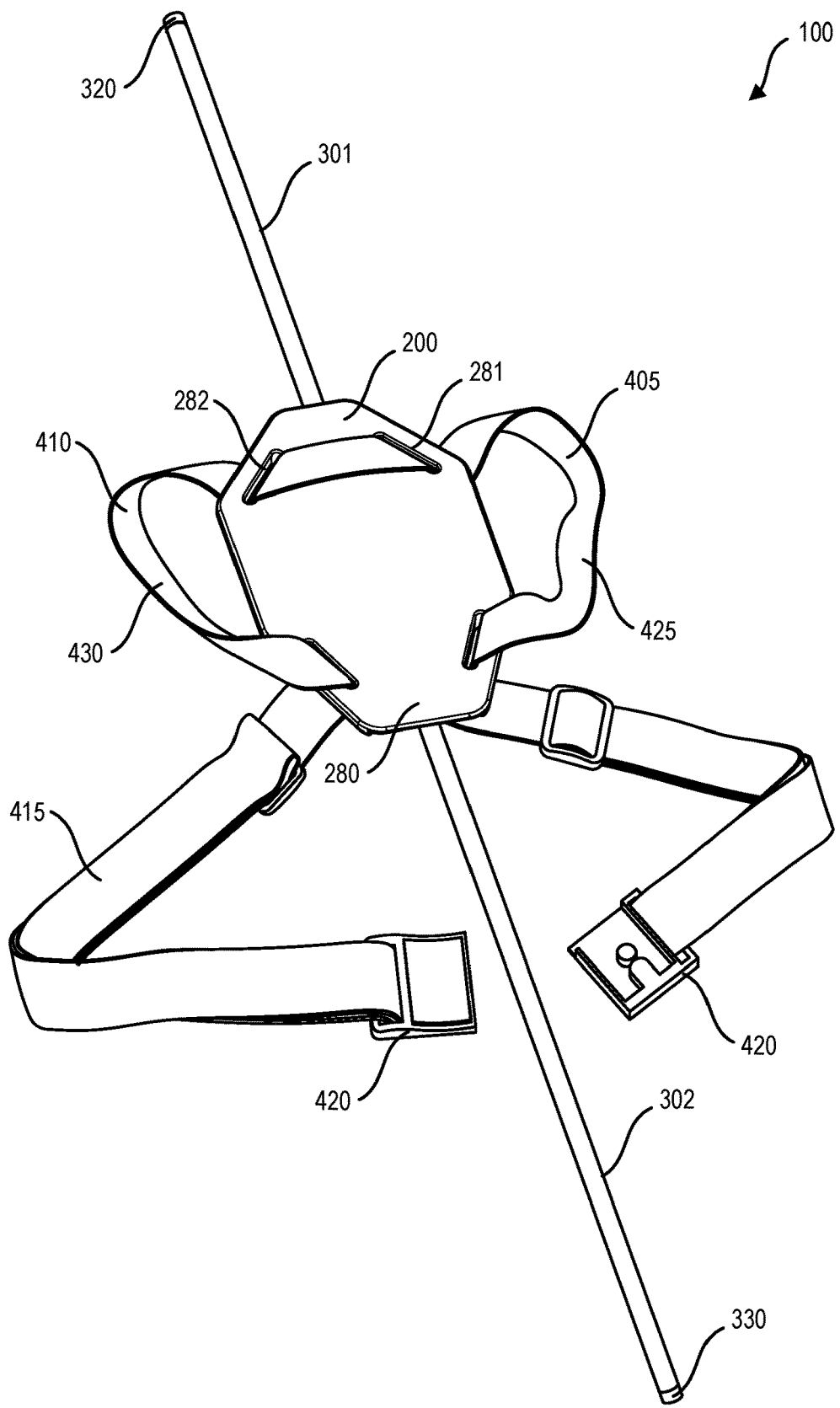
FIG. 2 shows a rear perspective view of the posture training device of FIG. 1.
Figure 3:
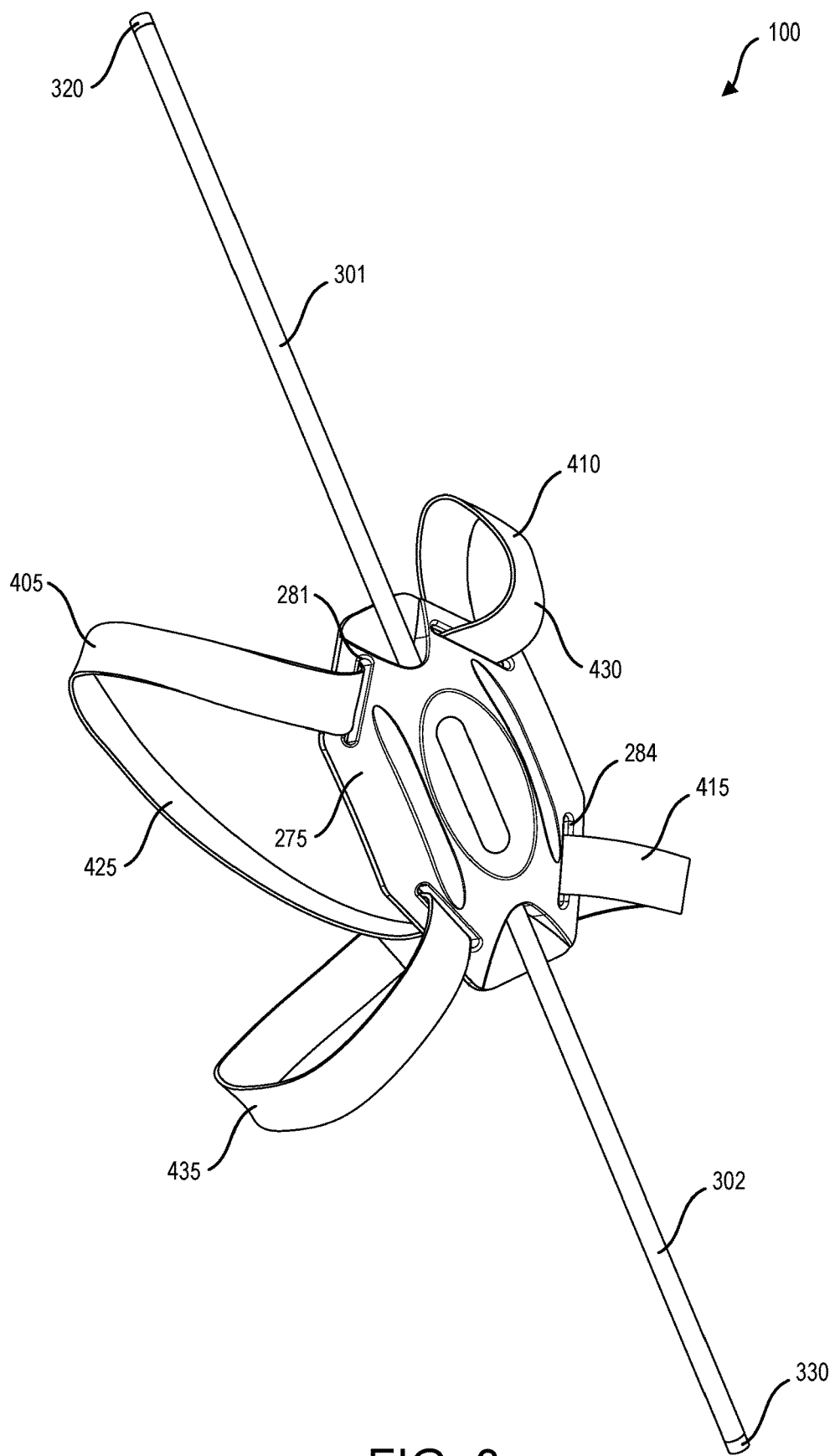
FIG. 3 shows a front perspective view of the posture training device of FIG. 1.

The posture training device 100 may include a strap 400. The strap 400 may secure the chassis 200 against the user's mid-back. The strap 400 may be a single strap or a plurality of straps. The strap 400 may include a first shoulder strap 405, a second shoulder strap 410, and a waist strap 415, as shown in FIGS. 1-3. The strap 400 may be woven through the strap slots (e.g. 281, 282, 283, 284) in the chassis 200 to form a first shoulder loop 425, a second should loop 430, and a waist loop 435. The first shoulder loop 425 may wrap around the user's left shoulder. The second shoulder loop 430 may wrap around the user's right shoulder. The waist loop 435 may wrap around the user's waist. The waist loop 435 may include a fastener 420, such as a buckle. The strap 400 may be adjustable in size.

When stowing the device 100, the strap 400 may be wrapped around the chassis 275 and rods (301, 302), as shown in FIG. 4. The strap may aid in securing the rods (301, 302) in the rod storage slots (245, 250).

The elements and method steps described herein can be used in any combination whether explicitly described or not. All combinations of method steps as described herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of 1-10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

As used herein, term "connected to" can describe a first component directly connected to a second component or a first component indirectly connected to a second component by way of one or more intervening components.

The methods and compositions of the present invention can comprise, consist of, or consist essentially of the essential elements and limitations described herein, as well as any additional or optional steps, components, or limitations described herein or otherwise useful in the art.

It is understood that the invention is not confined to the particular construction and arrangement of parts herein illustrated and described, but embraces such modified forms thereof as come within the scope of the claims.

The foregoing description has been presented for purposes of illustration and description. It is not intended to be exhaustive or to limit the claims to the embodiments disclosed. Other modifications and variations may be possible in view of the above teachings. The embodiments were chosen and described to explain the principles of the invention and its practical application to enable others skilled in the art to best utilize the invention in various embodiments and various modifications as are suited to the particular use contemplated. It is intended that the claims be construed to include other alternative embodiments of the invention except insofar as limited by the prior art.

What is claimed is:

1. A shapable posture training device comprising:
   a chassis comprising a pliable body configured to be worn against a thoracic spine region;
   a shapable member disposed within the pliable body, the shapable member extending from a top portion of the pliable body to a bottom portion of the pliable body;
   a first rod extending beyond a top side of the chassis, the first rod having a first centerline; and a second rod extending beyond a bottom side of the chassis, the second rod having a second centerline, wherein a relative rod angle is formed by an intersection of the first centerline and the second centerline, the shapable member being bendable to achieve a relative rod angle greater than 180 degrees in a first configuration and less than 180 degrees in a second configuration.

2. The shapable posture training device of claim 1, further comprising:
a first opening in the top portion of the pliable body; and
a first rod receiver disposed within the first opening,
wherein the first rod is insertable into and removable from a first bore of the first rod receiver.

3. The shapable posture training device of claim 2, further comprising:
a second opening in the bottom portion of the pliable body; and
a second rod receiver disposed within the second opening,
wherein the second rod is insertable into and removable from a second bore of the second rod receiver.

4. The shapable posture training device of claim 1, further comprising:
a first rod receiver disposed in the pliable body; and
a first magnet within the first rod receiver,
wherein the first magnet exerts a magnetic force on a ferrous portion of the first rod.

5. The shapable posture training device of claim 1, further comprising:
a second rod receiver disposed in the pliable body; and
a second magnet within the second rod receiver,
wherein the second magnet exerts a magnetic force on a ferrous portion of the second rod.

6. The shapable posture training device of claim 1, further comprising:
a first rod storage slot integrated into a front surface of the pliable body, the first rod storage slot configured to receive and retain the first rod; and
a second rod storage slot integrated into the front surface of the pliable body, the second rod storage slot configured to receive and retain the second rod.

7. The shapable posture training device of claim 1, further comprising a strap comprising:
a first shoulder loop extending from an upper left portion of the pliable body to a lower left portion of the pliable body;
a second shoulder loop extending from an upper right portion of the pliable body to a lower right portion of the pliable body; and
a waist loop extending from the lower left portion of the pliable body to the lower right portion of the pliable body.

8. The shapable posture training device of claim 1, further comprising:
a first rod receiver disposed in the pliable body between a horizontal midplane and the top side of the chassis, the first rod receiver comprising a first bore and a first slot; and
a second rod receiver disposed in the pliable body between the horizontal midplane and the bottom side of the chassis, the second rod receiver comprising a second bore and a second slot,
wherein the shapable member connects the first rod receiver to the second rod receiver,
wherein a first end of the shapable member is inserted into the first slot in the first rod receiver and a second end of the shapable member is inserted into the second slot of the second rod receiver.

9. A shapable posture training device comprising:
a chassis configured to be worn against a thoracic spine region, the chassis comprising:
a pliable body having a top side, a bottom side, a left side, a right side, and a horizontal midplane;
a first rod receiver disposed in the pliable body between the horizontal midplane and the top side of the pliable body, the first rod receiver comprising a first bore and a first slot; and
a second rod receiver disposed in the pliable body between the horizontal midplane and the bottom side of the pliable body, the second rod receiver comprising a second bore and a second slot;
a shapable member within the pliable body, the shapable member extending from the first slot to the second slot, the shapable member bendable to alter an alignment of a first centerline of the first bore and a second centerline of the second bore; and
a rear channel in a rear surface of the pliable body, the rear channel located between the first rod receiver and the second rod receiver, the rear channel comprising extending horizontally in the rear surface of the pliable body.

10. The shapable posture training device of claim 9, further comprising:
a first beam extending lengthwise along a rear surface of the pliable body from a top portion of the pliable body toward a middle portion of the pliable body, the first beam covering the first rod receiver with a pliable material; and
a second beam extending lengthwise along a rear surface of the pliable body from a bottom portion of the pliable body toward a middle portion of the pliable body, the second beam covering the second rod receiver with a pliable material,
wherein the rear channel is located between the first beam and the second beam.

11. The shapable posture training device of claim 9, further comprising:
a first pocket in the rear surface of the pliable body; and
a second pocket in the rear surface of the pliable body,
wherein the rear channel extends from the first pocket to the second pocket.

12. The shapable posture training device of claim 9, further comprising:
a first magnet disposed within the first bore;
a second magnet disposed within the second bore;
a first rod configured to slide into the first rod receiver, the first rod comprising a first ferrous end portion configured to mate against the first magnet within the first bore; and
a second rod configured to slide into the second rod receiver, the second rod comprising a second ferrous end portion configured to mate against the second magnet within the second bore.

13. The shapable posture training device of claim 9, wherein an angle formed at an intersection of the first centerline of the first bore and the second centerline of the second bore can range from less than 175 degrees to greater than 185 degrees.

14. The shapable posture training device of claim 9, further comprising:

a first strap slot between the horizontal midplane and the top side and between a vertical midplane and a left side;

a second strap slot between the horizontal midplane and the top side and between the vertical midplane and a right side;

a third strap slot between the horizontal midplane and the bottom side and between the vertical midplane and the left side; and a fourth strap slot between the horizontal midplane and the bottom side and between the vertical midplane and the right side.

15. The shapable posture training device of claim 14, further comprising a strap portion woven through the first strap slot, the second strap slot, the third strap slot, and the fourth strap slot to form a first shoulder loop, a second shoulder loop, and a waist loop.

16. The shapable posture training device of claim 9, further comprising:
   a first rod configured to removably insert into the first bore of the first rod receiver; and
   a second rod configured to removably insert into the second bore of the second rod receiver.

17. A shapable posture training device comprising:
   a chassis configured to be worn against a thoracic spine region, the chassis comprising:
      a pliable body;
      a shapable member within the pliable body;
      a first rod receiver disposed in the pliable body between a horizontal midplane and a top side of the pliable body, the first rod receiver comprising a first bore; and
      a second rod receiver disposed in the pliable body between the horizontal midplane and a bottom side of the pliable body, the second rod receiver comprising a second bore,
   wherein the shapable member connects the first rod receiver to the second rod receiver, and
   wherein the shapable member is bendable to alter a relative bore angle formed between a first centerline of the first bore and a second centerline of the second bore;
   a first rod configured to insert into the first bore of the first rod receiver and extend beyond the top side of the chassis, the first rod having a length greater than a length of the pliable body; and
   a second rod configured to insert into the second bore of the second rod receiver and extend beyond the bottom side of the chassis, the second rod having a length greater than the length of the pliable body.

18. The shapable posture training device of claim 17, further comprising a strap portion extending through a plurality of slots in the chassis to form a first shoulder loop, a second shoulder loop, and a waist loop.

19. The shapable posture training device of claim 17,
   wherein the shapable member is a metal strip that extends from a first slot in the first rod receiver to a second slot in the second rod receiver, and
   wherein the shapable member can be bent to alter the relative bore angle from about 135 degrees to about 225 degrees.

20. The shapable posture training device of claim 17, further comprising:
   a first magnet in the first rod receiver;
   a second magnet in the second rod receiver;
   a first ferrous portion located at a first end of the first rod; and
   a second ferrous portion located at a second end of the second rod.

* * * * *